(12) United States Patent
Schick et al.

(10) Patent No.: US 6,972,411 B2
(45) Date of Patent: Dec. 6, 2005

(54) METHOD OF EVENT DETECTION FOR INTRAORAL IMAGE SENSOR

(75) Inventors: David B. Schick, Flushing, NY (US); Stan Mandelkern, Teaneck, NJ (US); Valeriy Armencha, White Plains, NY (US)

(73) Assignee: Schick Technologies, Inc., Long Island City, NY (US)

(*) Notice: Subject to any disclaimer, the term of this patent is extended or adjusted under 35 U.S.C. 154(b) by 379 days.

(21) Appl. No.: 10/315,207

(22) Filed: Dec. 10, 2002

(65) Prior Publication Data

US 2004/0065836 A1 Apr. 8, 2004

Related U.S. Application Data

(60) Provisional application No. 60/415,716, filed on Oct. 3, 2002.

(51) Int. Cl.$^7$ .............................. G01T 1/20; G01T 1/24
(52) U.S. Cl. ........................ 250/370.11; 250/370.09; 250/370.01
(58) Field of Search .................. 250/370.09, 370.08, 250/370.01, 370.11; 378/98.8

(56) References Cited

U.S. PATENT DOCUMENTS

| | | | |
|---|---|---|---|
| 4,082,953 A | 4/1978 | Krause et al. | 250/413 |
| 4,160,997 A | 7/1979 | Schwartz | 358/93 |
| 4,494,950 A | 1/1985 | Fischell | 604/66 |
| 4,575,805 A | 3/1986 | Moermann et al. | 364/474 |
| 4,629,424 A | 12/1986 | Lauks et al. | 433/6 |
| 4,633,304 A | 12/1986 | Nagasaki | 358/98 |
| 4,658,669 A | 4/1987 | Nishikawa | 74/531 |
| 4,835,410 A | 5/1989 | Bhagwat et al. | 307/64 |
| 4,858,001 A | 8/1989 | Milbank et al. | 358/98 |
| 4,981,141 A | 1/1991 | Segalowitz | 128/696 |
| 4,987,897 A | 1/1991 | Funke | 128/419 |
| 5,113,859 A | 5/1992 | Funke | 128/419 |
| 5,115,307 A | 5/1992 | Cooper et al. | 358/98 |
| 5,212,476 A | 5/1993 | Maloney | 340/825.19 |
| 5,231,653 A | 7/1993 | Pfeiler et al. | 378/91 |
| 5,233,662 A | 8/1993 | Christensen | 381/70 |
| 5,257,184 A | 10/1993 | Mushabac | 364/413.28 |
| 5,264,935 A | 11/1993 | Nakajima | 358/181 |
| 5,373,852 A | 12/1994 | Harrison et al. | 128/733 |
| 5,434,418 A | 7/1995 | Schick | 250/370.11 |
| 5,454,022 A | 9/1995 | Lee et al. | 378/98.8 |
| 5,471,515 A | 11/1995 | Fossum et al. | 377/60 |
| 5,471,518 A | 11/1995 | Barber et al. | 379/58 |
| 5,510,623 A * | 4/1996 | Sayag et al. | 250/370.11 |
| 5,513,252 A * | 4/1996 | Blaschka et al. | 378/98.8 |
| 5,514,873 A | 5/1996 | Schulze-Ganzlin et al. | 250/394 |
| 5,527,261 A | 6/1996 | Monroe et al. | 600/109 |
| 5,551,953 A | 9/1996 | Lattin et al. | 604/20 |
| 5,712,482 A | 1/1998 | Gaiser et al. | 250/363.08 |
| 5,745,165 A | 4/1998 | Atsuta et al. | 348/65 |
| 5,873,814 A | 2/1999 | Adair | 600/109 |
| 5,879,289 A | 3/1999 | Yarush et al. | 600/179 |
| 5,880,826 A | 3/1999 | Jung et al. | 356/73 |
| 5,908,294 A | 6/1999 | Schick et al. | 433/29 |
| 6,069,935 A | 5/2000 | Schick et al. | 378/98.8 |

(Continued)

*Primary Examiner*—Albert Gagliardi
(74) *Attorney, Agent, or Firm*—Fitzpatrick, Cella, Harper & Scinto

(57) ABSTRACT

A method of determining that radiation is incident upon a radiation sensor comprising a plurality of radiation sensitive pixels includes the steps of monitoring an amount of current drawn by the pixels, and generating a signal indicating a presence of incident radiation which the amount of current exceeds a predetermined amount.

16 Claims, 4 Drawing Sheets

U.S. PATENT DOCUMENTS

| | | | |
|---|---|---|---|
| 6,132,211 A | 10/2000 | Peithman | 433/29 |
| 6,134,298 A | 10/2000 | Schick et al. | 378/98.8 |
| 6,149,300 A | 11/2000 | Greenway et al. | 378/191 |
| 6,186,944 B1 | 2/2001 | Tsai | 600/200 |
| 6,295,337 B1 | 9/2001 | Thevenin et al. | 378/117 |
| 6,320,934 B1 | 11/2001 | Carroll et al. | 378/98.8 |
| 6,339,633 B1 | 1/2002 | Hull et al. | 378/91 |
| 6,402,707 B1 | 6/2002 | Ernst | 600/590 |
| 6,404,854 B1 | 6/2002 | Carroll et al. | 378/98.8 |
| 6,797,960 B1 * | 9/2004 | Spartiotis et al. | 250/370.09 |
| 2001/0052930 A1 | 12/2001 | Adair et al. | 348/65 |
| 2001/0055368 A1 | 12/2001 | Carroll | 378/189 |
| 2002/0150214 A1 | 10/2002 | Spahn | 378/189 |
| 2003/0185338 A1 | 10/2003 | Dafni et al. | 378/15 |

* cited by examiner

METHOD OF EVENT DETECTION FOR INTRAORAL IMAGE SENSOR

CROSS-REFERENCE TO RELATED APPLICATION

This application claims the benefit of U.S. provisional application No. 60/415,716, filed Oct. 3, 2002.

BACKGROUND OF THE INVENTION

1. Field of the Invention

This invention relates to a filmless dental radiography system, and more particularly to a method of detecting the presence of radiation incident on a filmless intraoral radiation sensor.

2. Description of the Related Art

Dentists and oral surgeons typically use x radiation to obtain images of their patient's teeth, mouths and gums to aid in diagnosis and treatment. In traditional oral and dental radiography, a cartridge containing photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth.

More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire development process, including the use of potentially harmful chemicals. In addition, because the images are generated electronically, they can be stored electronically in a computer database.

Examples of filmless dental radiography systems include those described in U.S. Pat. No. 4,160,997 to Robert Schwartz and U.S. Pat. No. 5,434,418 to David Schick.

One of the problems associated with filmless intraoral sensors is the so-called event detection problem, i.e. determining when the sensor has been exposed to radiation and therefore contains image data which may be read-out. More particularly, since filmless detection systems are typically manufactured and sold separately from, and not synchronized with, the radiation source (such as, for example, the x-ray generator), the radiation sensor must have some mechanism or technique for determining when it has been exposed to x-rays, so that it knows when to read out the image data.

One way to solve this problem, of course, would be to synchronize the radiation source with the sensor, such as for example by sending a special signal from the radiation source to the sensor or signal when the radiation source is triggered. This approach, however, requires that the sensor and radiation source be manufactured and sold by the same entity, or by entities in concert, or that complicated aftermarket equipment that interfaces to the radiation source be used. None of those options are practicable.

U.S. Pat. No. 6,069,935 describes a conventional option for solving the event detection problem, in which the sensor includes several discrete event trigger diodes which detect incident radiation and output a signal indicating the same. The outputs of the diodes may be monitored by a computer to determine the start and end of the x-ray exposure. This method allows for accurate exposures to be taken without the need to synchronize the x-ray source with the computer. However, while generally good for its intended applications, this solution has some drawbacks. Most notably, the incorporation of event trigger diodes into the sensors lowers manufacturing yield, since a malfunction in any of the event detection diodes will cause the entire sensor to malfunction. Also, the diodes themselves may be blocked by some radiation impervious portion of the material under test, or may be out of the field of the radiation beam entirely.

Another approach to event detection described in U.S. Pat. No. 6,069,935 entails continuously reading out from the sensor frames of data representing the entirety of the data contained therein, and determining whether the sensor was exposed to radiation by examining the frames of data. This approach is highly effective, and provides a reliable way of solving the event detection problem without needing to synchronize source and sensor, and without needing to use event detection diodes. However, despite the advantages of this technique, a limitation is that it requires that the sensor be read out continuously, and therefore consumes a relatively high amount of electrical power. Thus, it is a less than optimal approach, particularly in situations in which power conservation is an important concern.

U.S. Pat. No. 6,404,845 B1 utilizes an approach in which the image sensor is monitored during a wait for exposure period. During this period, the values of reference pixels are compared to a threshold level, and when a predetermined number of reference pixels exceed the threshold, a decision is made that exposure has started. This approach, however, also consumes a high amount of power, and is therefore sub-optimal.

There is a need, therefore, for a filmless dental radiography system in which the sensor can detect automatically the presence of radiation, without needing to synchronize the sensor and the radiation source, and without needing to incorporate event detection diodes into the sensor.

SUMMARY OF THE INVENTION

One object of the present invention is to provide a filmless dental radiography system having an intraoral sensor which can perform efficient and reliable event detection.

Another object of the present invention is to provide a filmless dental radiography system having an intraoral sensor which can perform efficient and reliable event detection without the use of event detection diodes.

Another object of the present invention is to provide a filmless dental radiography system in which event detection is effected in a power-efficient manner.

In one embodiment of the present invention, a method is provided for determining that radiation is incident upon a radiation sensitive sensor comprising a plurality of radiation sensitive pixels. The method is carried out by monitoring an amount of current drawn by the pixels, and generating a signal indicating the presence of incident radiation when the amount of current drawn by the pixels exceeds a predetermined amount.

In another embodiment of the present invention, a radiation sensitive sensor comprises a plurality of radiation sensitive pixels, and an event detection circuit that determines that radiation is incident upon the pixels. The determination is made based upon an amount of electrical current drawn by the pixels.

In yet another embodiment of the present invention, a radiation sensitive sensor comprises means for generating an amount of electrical charge corresponding to an intensity of radiation incident on the sensor, and means for determining that radiation is incident on the generating means. The determination is made based upon an amount of electrical charge drawn by the generating means.

DETAILED DESCRIPTION OF THE PREFERRED EMBODIMENTS

Figure 1:
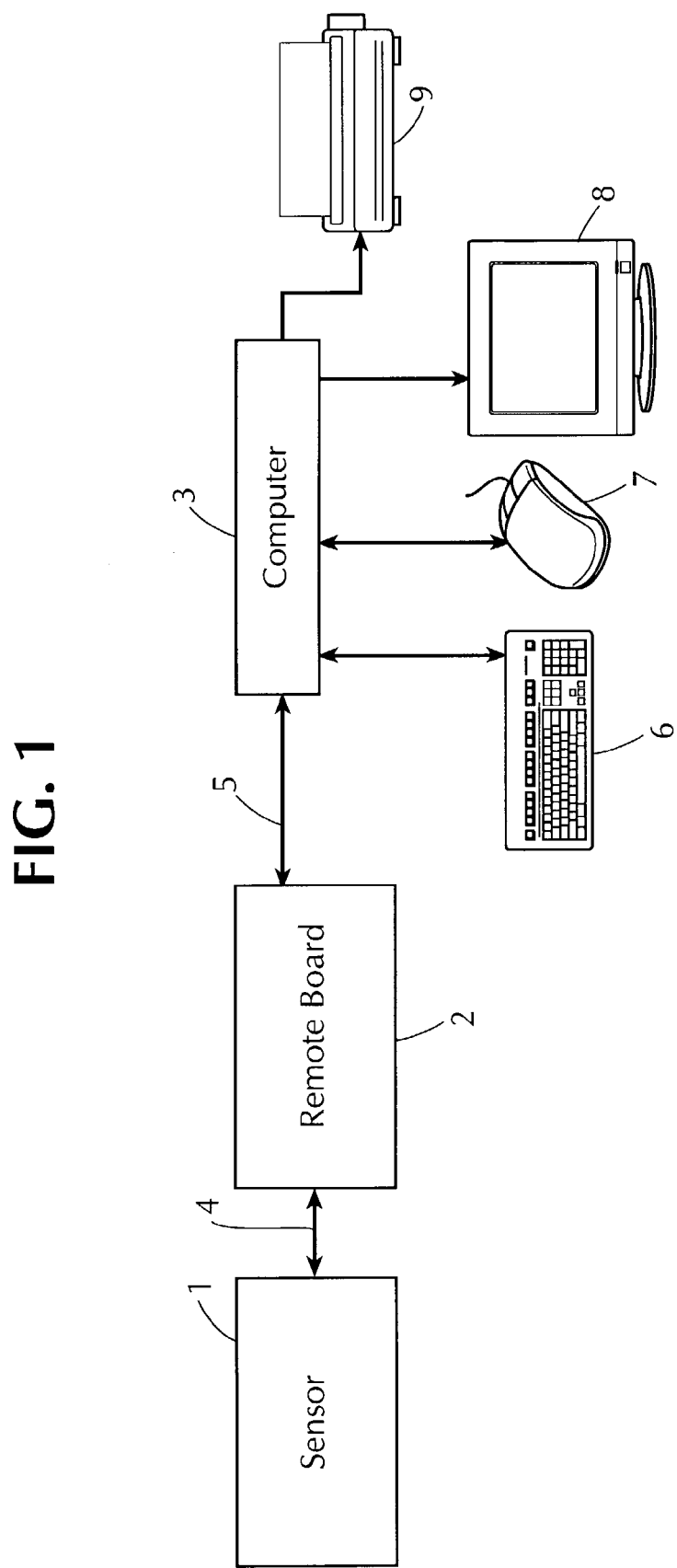
FIG. 1 is a block level illustration of one embodiment of the dental radiography system of the present invention.

A first embodiment of a filmless dental radiography system in accordance with the present invention is depicted in FIG. 1. As can be seen, the system includes an electronic sensor 1, a remote board 2 and a host computer 3. The sensor 1 communicates with the remote board 2 over a bi-directional wired link 4, and the remote board 2 communicates with the computer 3 over a bi-directional wired link 5. The remote board 2 performs many control and processing functions, which may include, among other things, controlling the operation of the sensor 1, reading out data from the sensor 1, effecting analog-to-digital conversion and processing the data read out of the sensor 1 into a form suitable for transmission to the host computer 3.

Figure 1A:
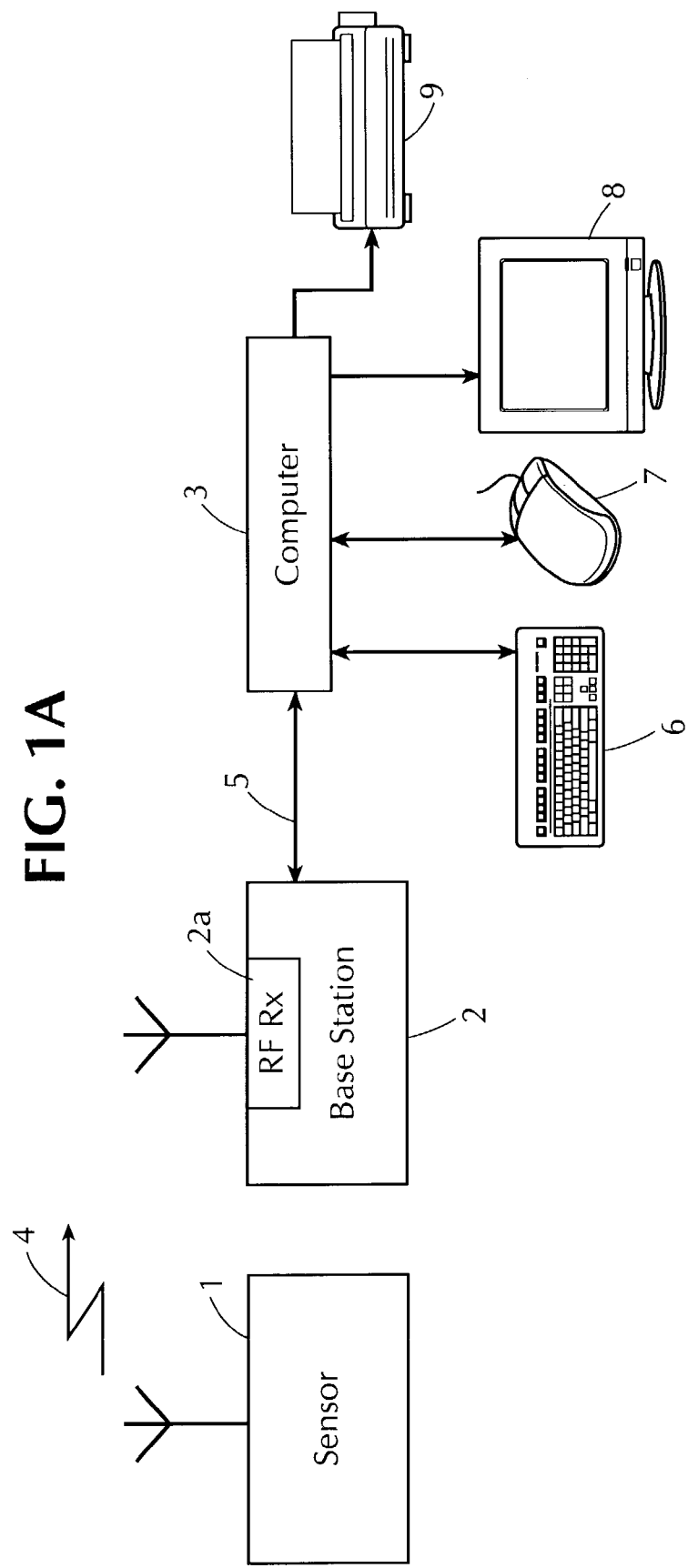
FIG. 1A is a block level illustration of another embodiment of the dental radiography system of the present invention.

An alternate embodiment of a filmless dental radiography system according to the present invention is depicted in FIG. 1A. This system includes an intraoral sensor 1, a base station 2 that includes a radio frequency (RF) receiver 2a and data output ports (not shown), and a host computer 3. The sensor 1 communicates with the RF receiver 2a of the base station 2, which is located outside the oral cavity, via wireless RF link 4, as will be discussed in greater detail below. The base station 2 communicates with the host computer 3 over a bi-directional wired link 5, and performs many or all of the functions performed by the remote board 2 described above.

In any case, the communication between the remote board or base station 2 and host computer 3 is preferably via the widely available and accessible Universal Serial Bus port, as described in U.S. Pat. No. 6,134,298 assigned to the assignee of the present invention and hereby incorporated by reference. Alternatively, communication with the host computer 3 may be via the computer's Peripheral Component Interconnect (PCI) bus, a high-speed Firewire bus, or via the computer's Industry Standard Architecture (ISA) bus. In such a case, a special purpose board normally would be housed in the host computer 3 to facilitate such communication. In any case, the communication between the sensor 1 and host computer 3 should be direct and nearly instantaneous.

The host computer 3 may be any conventional desktop, tower, laptop or notebook computer, equipped with software for processing the data provided to it. The computer 3 is either connected to or has built in one or more input devices, such as a keyboard 6 or a mouse 7, and one or more output devices, such as a monitor 8 or a printer 9. These devices allow the user to control the operation of the system, and to view the dental images that the system creates. The computer might also include or be connected to some type of storage device (not shown), such as a hard drive, for permanent storage of the images in patient files.

Figure 2:
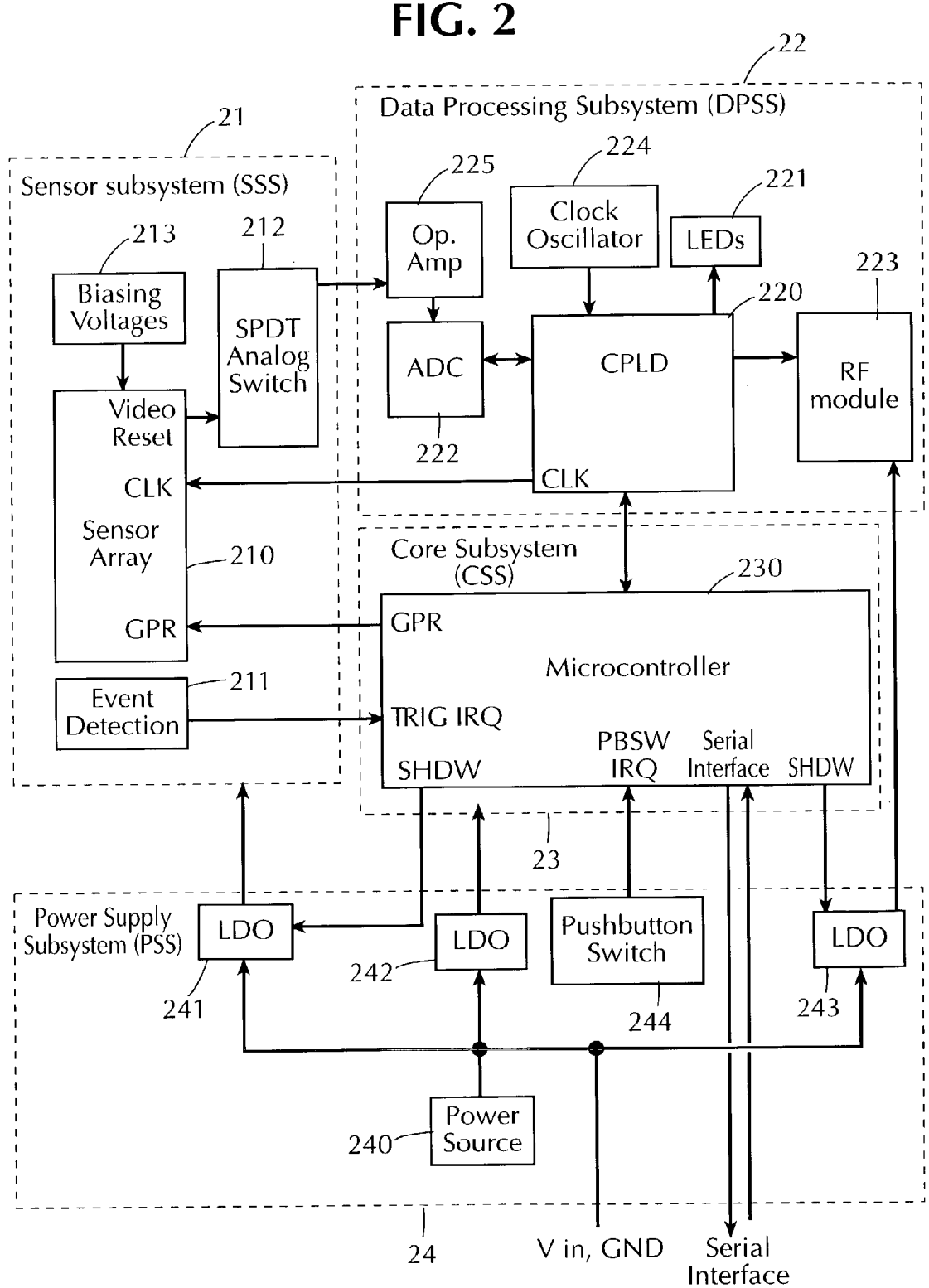
FIG. 2 is a block level illustration of one embodiment of the intraoral sensor of the present invention.

It will be readily appreciated that the techniques of the present invention have applicability to both the embodiment of FIG. 1 and the embodiment of FIG. 1A In any event, an embodiment of the intraoral sensor 1 is depicted schematically in FIG. 2. The sensor 1 in this embodiment is divided into four subsystems: a Sensor Subsystem (SSS) 21 that includes the actual sensor array 210, an event detection module 211, a single-pole double-throw analog switch 212 and a biasing voltages module 213; a Data Processing Subsystem (DPSS) 22 that includes a complex programmable logic device (CPLD) 220 (which among other things provides clock signals CLK to the sensor array 210), light emitting diodes (LEDs) 221, a 10 MHz clock oscillator 224 and operational amplifiers (op amps) 225, and in the FIG. 1A embodiment an analog-to-digital converter (ADC) 222 and a radio frequency (RF) module 223, and a Core Subsystem (CSS) 23 that includes a microcontroller 230. In the embodiment of FIG. 1A, the sensor 1 may also include a Power Supply Subsystem (PSS) 24 that includes a power source 240 (such as for example a replaceable battery). Alternatively, such as in the FIG. 1 embodiment, the sensor might receive its power from the host computer 3 or remote board 2.

All components are encapsulated in a hermetically sealed housing so as to be suitable for insertion into the human mouth. The sensor housing is opaque to visible light but radiolucent, i.e. pervious to x-rays. Preferably, the sensor is impervious to liquid penetration and resistant to mechanical damage as could occur if a patient bit on the device or if the device were dropped from standing height. The package is typically scant on available space since the sensor is preferably less than 6 mm thick. The various components must therefore be selected with an eye towards miniaturization. In a preferred embodiment, light emitting diodes (LEDs) 221 on the surface of the sensor packaging comprise a portion of DPSS 22, and are used to indicate status. The sensor body is manufactured from a material such as plastic, to allow carrier waves to be transmitted without interference.

The sensor array 210 preferably comprises a CMOS APS array, such as for example a CMOS APS array of the type described in U.S. Pat. No. 5,471,515 and U.S. Pat. No. 6,134,298 each of which is hereby incorporated by reference. Each pixel in the APS array includes one or more active transistors which perform gain or buffering functions. The sensor array 210 may alternatively be a CCD, or some other type of solid state device capable of converting electromagnetic radiation into electrical signals. As used herein, the term radiation broadly encompasses all waves in the electromagnetic spectrum. In any case, the sensor array 210 may additionally comprise on top of the CMOS APS array, CCD or other solid state device, a scintillator layer which converts x-rays into visible light, and might further include disposed beneath the scintillator layer a fiber optic faceplate.

The remaining components of the sensor, including the remaining electronics of SSS 21 and the electronics of DPSS 22, CSS 23 and PSS 24, comprises all of the circuitry necessary to control the exposure and readout of an image, and to provide and/or manage the requisite electrical power. The specifics of such electronics will vary with the nature of the sensor array 210. In the preferred embodiment illustrated in FIG. 2, these electronics perform the functions of row driver circuitry, reset driven circuitry, column signal chain circuitry, column shift register circuitry and timing and control circuitry, among other things.

The novel event detection technique of the present invention will now be described with reference to FIG. 2. The novel technique of the present invention is based upon the observation that, in an imaging array, such as for example in a CMOS imaging array or a CCD imaging array, the magnitude of current drawn by each pixel is itself sensitive to the presence of radiation on the pixel, such that the pixels draw much more current when exposed to radiation and much less when not exposed to radiation. In an APS array, this current is the photo-induced current which flows through each diode in the array. In a CCD, there is a similar phenomenon at the substrate bias or similar point. In either case, the amount of current drawn may be used as a means of event detection.

Figure 3:
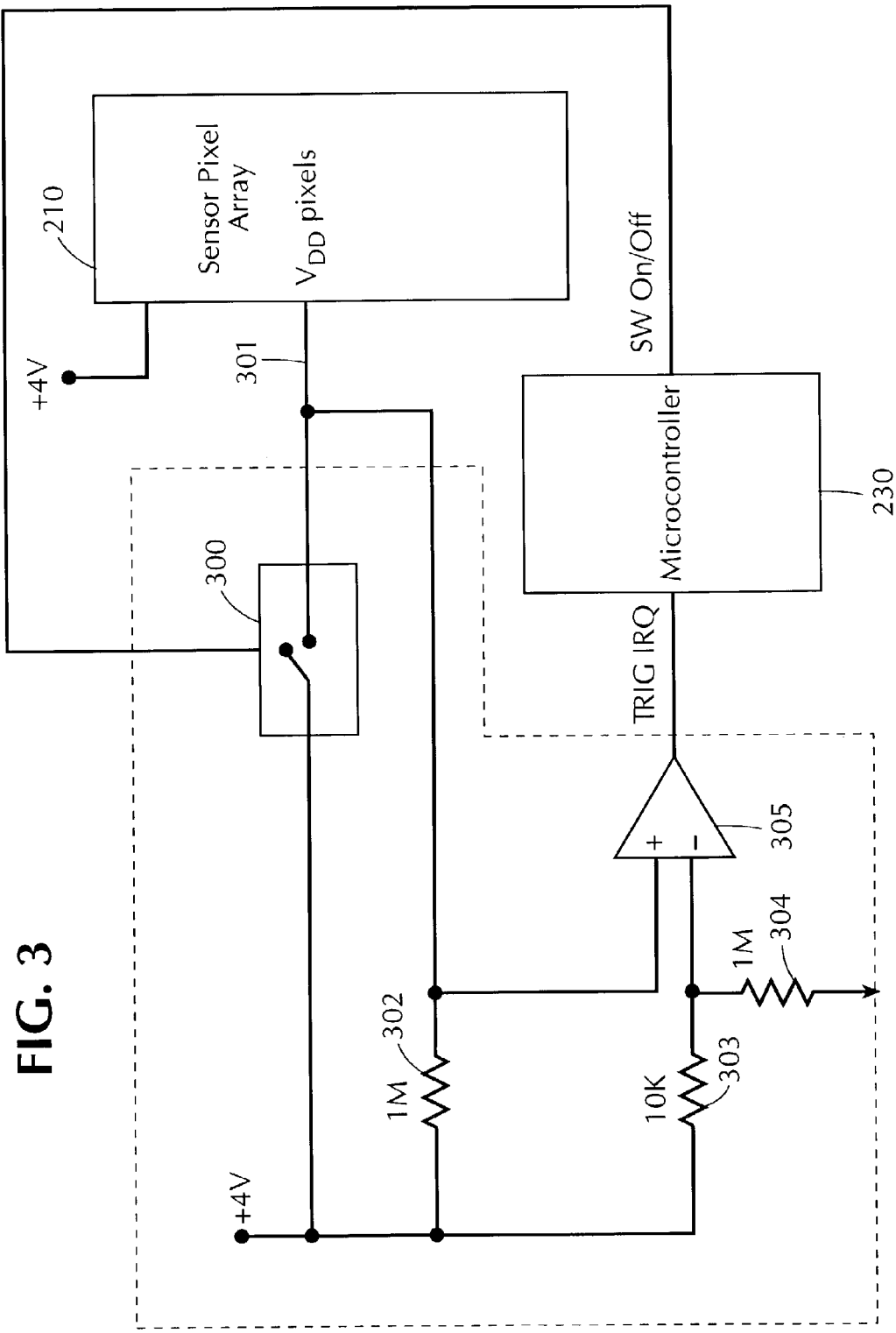
FIG. 3 is a schematic of a novel event detection circuit in accordance with one embodiment of the present invention.

The details of a suitable circuit for such an event detection module 211 are shown in FIG. 3. In FIG. 3, a bias voltage of +4V is connected to the input of a normally open switch 300, the output of which is connected to a supply line 301 that feeds the VDD input of each pixel. The +4V bias voltage is also connected to the supply line 301 through a large (1MΩ) resistor 302 that is used as a current sensing device. When there is no radiation incident on the sensor array 210, the switch 300 is open and a very small current is drawn by the supply line 301 through the current sensing resistor 302. The presence of x-ray radiation causes a step increase in the magnitude of the current drawn, which increase is sensed by resistor 302 to cause a corresponding step change in the voltage across it. This voltage change is detected by a comparator 305, which in turn generates a trigger interrupt request (TRIG IRQ) signal which it sends to the microcontroller 230. The TRIG IRQ signal indicates the presence of radiation, and causes the microcontroller 230 to generate a SW ON/OFF signal that closes the switch 300, and also to commence its routine to acquire the image from the sensor array 210. After the image acquisition routine is complete, the microcontroller re-opens the switch 300 and again enters the mode of waiting for another TRIG IRQ signal.

The magnitude of the step increase necessary to cause the comparator 305 to generate an TRIG IRQ signal is dependent upon the amounts of current drawn by the supply line 301 in the dark (non-irradiated) state and the irradiated state, the value of the current sensing resistor 302 and the values of resistors 303 and 304 which function as a voltage divider to generate a reference voltage. In the exemplary embodiment depicted in FIG. 3, the voltage divider is comprised of a 10 KΩ resistor 303 and a 1 MΩ resistor 304, the supply line 301 draws about 6 nA in the dark state and an TRIG IRQ signal is generated when there is a step increase to about 60 nA, representing a one order of magnitude increase in current.

During the image acquisition routine, analog data representing a captured image are read-out of the sensor array 210, conditioned by op-amps 225, converted to digital data by an analog-to-digital (ADC) 222 and provided to RF module 223 via the CPLD 220, all under the control of the microcontroller 230. The microcontroller 230 may be any suitable processor, such as for example a chip that comprises a reduced instruction set computer (RISC) and memory. An example of a suitable microcontroller is the MSP430F1121-A part manufactured and sold by Texas Instruments. The CPLD may be any appropriately programmed logic array of sufficient complexity, such as for example the Cool Runner part manufactured and sold by Xilinx.

In the FIG. 1A embodiment the RF module 223, which may incorporate for example a Maxim MAX2750EUA voltage-controlled oscillator, transmits digital image data via an antenna and a wireless link. A high reliability RF link is essential since the data must be transmitted from the sensor from within a patient's mouth. Furthermore, because the amount of image data set is typically large, and transmission preferably should be nearly instantaneous, a high-speed link is required. The data are transmitted in digital form to ensure error-free transmission, although transmission of analog data is also possible.

In the CPLD 220, the native signal is divided into packets and encoded to Manchester format. In the RF module 223, a carrier is modulated with the resultant digital signal using frequency shift keying and transmitted at a frequency compliant with European and U.S. regulatory requirements. The effective transmission range is preferably at least ten feet, allowing clinicians freedom in where they choose to place the receiver. Preferably, RF module 223 transmits periodic carrier bursts to allow the host computer 3 to gauge the RF link status and insure that the sensor 1 is ready for use. The RF receiver 2a in base station 2 demodulates the modulated carrier to restore the original base band signal. Control logic may be implemented to facilitate operations such as the Manchester decoding, digital filtering, packet decoding and the suppression of unwanted signals. These steps help assure reliable communication between the base station and sensor as communication failures could result in unnecessary patient radiation exposure.

In the FIG. 1A embodiment, PSS 23 includes power source 240, such as a replaceable battery 240 having sufficient service life which can provide enough power to capture at least a full-mouth series of x-ray images (typically eighteen exposures), and preferably several full-month series of images, when the novel techniques of the present invention are implemented. Suitable types of batteries include, but are not limited to, nickel-cadmium, nickel-metal-hydride, lithium manganese dioxide and lithium ion. Other options for the power source 240 are also possible, such as for example an ultra cap device.

In the embodiment of FIG. 1A, the sensor 1 when not in use is kept in the base station 2. In an embodiment in which the sensor utilizes a rechargeable battery, the base station 2 serves to electrically recharge it. Preferably, the base station 2 can accept sensors of varying sizes (such as, for example, size 0, size 1 and size 2 sensors), and may also be configured to accept multiple sensors.

The base station 2 interfaces with the sensor via serial interface 245, and can be constructed to configure and perform diagnostics on the sensor 1. Such diagnostics are initiated by the base station 2 sending to the sensor 1 a SI IRQ. More specifically, a diagnostic program may be run on the sensor and the resultant data generated by the diagnostics operation may be provided to the base station 2

Communication between the sensor 1, remote board or base station 2 and host computer 3 may be controlled by specialized firmware and software residing on the sensor 1 (more specifically, in the memory of the microcontroller 230), base station 2 and host computer 3. The data may be exported from the base station 2 using one or more of a multitude of commonly used ports, including the USB. In a preferred embodiment, the USB not only provides data output capability, but also supplies power to the base station. Power to the base station could of course be achieved through alternative means as will be apparent to those skilled in the art. USB management may be handled by the base station as well.

It is understood that the above description and drawings are illustrative of the present invention and detail contained therein are not to be construed as limitations thereon. Changes in components, procedure and structure may be made without departing from the scope of the present invention as defined in the following claims.

What we claim is:

1. A method of determining that radiation is incident upon a radiation sensitive sensor comprising a scintillator that converts x-ray radiation to visible light radiation and a plurality of pixels sensitive to the visible light radiation, said method comprising the steps of
    monitoring an amount of current drawn by the plurality of pixels;
    generating a signal indicating a presence of incident radiation when the visible light radiation causes the amount of current drawn by the plurality of pixels to exceed a predetermined amount.

2. The method according to claim 1, wherein the amount of current drawn by the plurality of pixels is measured using a resistor.

3. The method according to claim 2, wherein the signal indicating the presence of incident radiation is generated by a comparator.

4. The method according to claim 3, wherein the comparator compares a voltage proportional to the amount of current drawn by the plurality of pixels with a fixed reference voltage.

5. The method according to claim 4, wherein the comparator generates a signal indicating the presence of incident radiation when the voltage proportional to the amount of current drawn by the plurality of pixels exceeds the fixed reference voltage.

6. The method according to claim 1, wherein said sensor is an intraoral sensor adapted to capture x-ray images inside of a patient's mouth.

7. The method according to claim 1, wherein said plurality of pixels comprises a CMOS active pixel sensor array.

8. A radiation sensitive sensor, comprising
    a scintillator that converts x-ray radiation to visible light radiation;
    a plurality of pixels sensitive to the visible light radiation;
    an event detection circuit that determines that radiation is incident upon said sensor when the visible light radiation causes an amount of electrical current drawn by said plurality of pixels to exceed a predetermined amount.

9. A sensor according to claim 8, wherein said event detection circuit includes:
    a resistor that senses an amount of current drawn by said plurality of pixels;
    a voltage divider that generates a reference voltage; and
    a comparator that generates a triggering signal when the voltage across said resistor exceeds the reference voltage.

10. A sensor according to claim 8, wherein said sensor is an intraoral sensor adapted to capture x-ray images inside of a patient's mouth.

11. A sensor according to claim 8, wherein said plurality of pixels comprises a CMOS active pixel sensor array.

12. A radiation sensitive sensor comprising:
    means for converting x-ray radiation to visible light radiation;
    means for generating an amount of electrical charge corresponding to an intensity of radiation incident on said sensor;
    means for determining that radiation is incident on said generating means when the visible light radiation causes an amount of electrical current drawn by said charge generating means to exceed a predetermined amount.

13. A radiation sensor according to claim 12, wherein said determining means includes:
    means for generating a reference voltage; and
    means for generating a voltage proportional to the amount of electrical current drawn by said charge generating means.

14. A radiation sensor according to claim 12, wherein said determining means includes:
    means for determining that radiation is incident on said charge generating means when the voltage proportional to the amount of current drawn by said charge generating means exceeds the reference voltage.

15. A radiation sensor according to claim 12, wherein said sensor is an intraoral sensor adapted to capture x-ray images inside of a patient's mouth.

16. A radiation sensor according to claim 12, wherein said charge generating means comprises a CMOS active pixel sensor array.

* * * * *